(12) United States Patent
Flohr et al.

(10) Patent No.: US 7,700,605 B2
(45) Date of Patent: Apr. 20, 2010

(54) 2-CYANO-PYRIMIDINES AND -TRIAZINES AS CYSTEINE PROTEASE INHIBITORS

(75) Inventors: Stefanie Flohr, Reinach (CH); Pascal Furet, Thann (FR); Patricia Imbach, Kaiseraugst (CH); Ulrich Hommel, Mullheim (DE); Hans-Ulrich Litshcer, Riehen (CH); Shirley Gil Parrado, Binningen (CH); Ulrich Hassiepen, Lorrach (DE); Johann Zimmermann, Auggen (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 11/995,994

(22) PCT Filed: Jul. 17, 2006

(86) PCT No.: PCT/EP2006/006999

§ 371 (c)(1),
(2), (4) Date: Jan. 17, 2008

(87) PCT Pub. No.: WO2007/009715

PCT Pub. Date: Jan. 25, 2007

(65) Prior Publication Data

US 2008/0214548 A1   Sep. 4, 2008

(30) Foreign Application Priority Data

Jul. 18, 2005 (GB) ................... 0514684.0

(51) Int. Cl.

| C07D 239/34 | (2006.01) |
| C07D 239/42 | (2006.01) |
| C07D 239/46 | (2006.01) |
| C07D 239/48 | (2006.01) |
| A61K 31/505 | (2006.01) |
| A61P 35/00  | (2006.01) |
| C07D 251/14 | (2006.01) |
| C07D 251/42 | (2006.01) |
| C07D 251/48 | (2006.01) |
| A61K 31/53  | (2006.01) |

(52) U.S. Cl. .................. 514/256; 514/269; 514/241; 514/246; 544/319; 544/326; 544/242; 544/180; 544/206; 544/219; 544/223

(58) Field of Classification Search ................ 544/319, 544/326, 242; 514/269, 256

See application file for complete search history.

(56) References Cited

OTHER PUBLICATIONS

Cecil Textbook of Medicine, edited by Bennet, J.C., and Plum F., 20th edition, vol. 1, 1004-1010, 1996.*
Freshney et al., Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
G.Dubin, Cellular and Molecular Life Sciences, vol. 62, 653-669, 2005.*

* cited by examiner

*Primary Examiner*—Venkataraman Balasubramanian

(57) ABSTRACT

The invention relates to compounds of the formula I

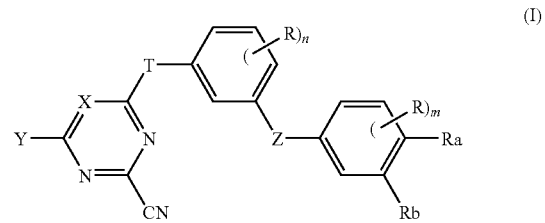

(I)

and salts thereof, to a process for their manufacture, to their use in the treatment of (especially cysteine protease, such as UCH-L3- and/or USP-2 dependent) diseases or for the manufacture of pharmaceutical formulations against these diseases, methods of treatment of warm-blooded animals comprising administering the compounds and/or their salts to said animals and pharmaceutical preparations, especially for the treatment of the diseases, comprising said compounds and/or salts.

8 Claims, No Drawings

2-CYANO-PYRIMIDINES AND-TRIAZINES AS CYSTEINE PROTEASE INHIBITORS

This application is a US National Phase filing of PCT/EP2006/006999 filed Jul. 17. 2006, and claims priority under 35 U.S.C. §119(a-d) to GB Patent Application Serial No. 0514684.0 filed July 18, 2005, the contents of which are incorporated herein by reference in their entirety.

SUMMARY OF THE INVENTION

The invention relates to 2-cyano-pyrimidine and -triazine derivatives and salts thereof, to a process for their manufacture, to their use in the treatment of (especially cysteine protease, such as UCH-L3- and/or USP-2 dependent) diseases or for the manufacture of pharmaceutical formulations against these diseases, methods of treatment of warm-blooded animals comprising administering the compounds and/or their salts to said animals and pharmaceutical preparations, especially for the treatment of the diseases, comprising said compounds and/or salts.

BACKGROUND OF THE INVENTION

De-ubiquitinating enzymes are a family of cysteine hydrolases which specifically cleave ubiquitin-derived substrates with the general structure Ub-L. Ub is ubiquitin(yl), L (at the C-terminus of Ub) can be any number of leaving groups ranging from small thiols and amines to Ub or other proteins. UCH-L3 is one of the members of this family of de-ubiquinating hydrolases.

Ubiquitin is a small (about 8.6 kDa) protein which is highly conserved and is especially well known for its role in targeting proteins for degradation to 26S protease. The protein has been reported to be involved in many cellular processes, inter alia cell cycle control, oncoprotein degradation, receptor function, apoptosis, regulation of transcription, stress responses, DNA repair, maintenance of chromatin structure, signaling pathways, antigen presentation and the degradation of abnormal proteins. The Ub-activating enzyme E1 is known to activate monomeric ubiquitin and forms a thioester bond with Ub C-terminus. The ligation of the Ub C-terminus to lysine side chains of acceptor proteins is then catalyzed by E2 (Ub-conjugating) and E3 (Ub ligase) enzyme families. The target proteins can be mono- or poly-ubiquitinated (the latter for example in the case of targeting for degradation by the 25S protease). Besides lysine side chains, the Ub C-terminus can also be found attached to α-amino groups in peptide bonds as all known Ub genes encode fusion proteins in which Ub is followed by a C-terminal extension.

Proteolytic processing at the Ub C-terminus is catalyzed by "DeUBiquinating enzymes" (DUBS). Numerous DUBs have been identified and fall into two families: Ubiquitin-specific Proteases (USPs) and Ubiquitin C-terminal Hydrolases (UCHs).

These enzymes all cleave the peptide bond at the C-terminus of Ub. UCH-L3 cleaves peptide extensions of up to 20 residues from Ub with high efficiency and low sequence preference. Larger folded extensions are not cleaved. Thus the UCHs are presumed to function in the regeneration of active Ub from adducts with small nucleophiles. UCH-L3 is expressed especially in hematopoietic cells. UCH-L3 is implicated in various disorders including immunological or proliferative diseases such as cancer, especially solid tumors, e.g. cancers of the colon, lung cancer or the like. The USP2 family includes a number of isoforms. UBP41 was found first in chicken, then other chicken isoforms were found (UBP46, UBP52, UBP66), and all show strong sequence similarity in the enzymatically active core region while they show differences by N- or C-terminal extension. Various ubiquitinylated test substrates have been shown to be hydrolyzed by these enzymes. DNA Sequences coding for human as well as murine USP2 homologues were identified, see Genbank. For human USP2, two isoforms have been described: a long transcript variant 1 and a short transcript variant 2. Abnormal USP function may lead to cancer and disease. For example, it has been shown that USP2a is elevated in prostate cancer cells, and inactivating the protease causes degradation of the enzyme fatty acid synthetase (which otherwise would help tumor cells to resist apoptosis and to survive under non-optimal growth conditions (see e.g. FOCUS, Apr. 16, 2004, Pat McCaffrey, News from Harvard Medical, Dental & Public Health Schools, Research Briefs, http://focus.hms.Harvard-.edu/2004/April16_2004/research_briefs.html. hUBP 41 was shown to be up- or down-regulated in a number of tumor cells, e.g. breast, uterus, ovary, kidney, colon, stomach, rectum and lung tumor cells.

Proliferative diseases and other diseases that depend on deviations of regulation e.g. in signaling and/or metabolic pathways are a very common cause of death in humans and also in other warm-blooded animals.

It is therefore the problem to be solved by the present invention to make available new inhibitors that are pharmacologically advantageous and/or especially are effective via new mechanisms of action.

GENERAL DESCRIPTION OF THE INVENTION

It is found now that 2-cyano-pyrimidine and -triazine derivatives compounds according to the present invention shown below provide a new class of compounds with pharmaceutically advantageous properties, especially regarding diseases that are dependent on cysteine proteases, in particular UCH-L3 and/or USP2.

By way of their ability to modulate, especially inhibit, the activity of cysteine proteases, especially UCH-L3 and/or USP2, these compounds are helpful in the treatment of a variety of diseases that depend on the activity of such cysteine proteases, especially those diseases mentioned in more detail below.

DETAILED DESCRIPTION OF THE INVENTION

The invention especially relates to a compound of the formula I,

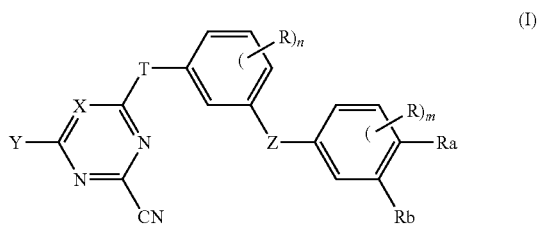

wherein
X is CH, CR or N;
Y is hydrogen or $C_1$-$C_7$-alkyl, $C_3$-$C_{10}$-cycloalkyl, $C_1$-$C_7$-alkyloxy, $C_3$-$C_{10}$-cycloalkyloxy or amino that is unsubstituted or substituted by one or two moieties selected from the group consisting of $C_1$-$C_7$-alkyl and $C_3$-$C_{10}$-cycloalkyl, where each $C_1$-$C_7$-alkyl and $C_3$-$C_{10}$-cycloalkyl mentioned as or forming part of a substituent Y mentioned so far is unsubstituted or substituted by halo, hydroxy, $C_1$-$C_7$-alkoxy, amino, N-mono- or N,N-di-($C_1$-$C_7$-alkyl)amino, nitro or cyano;

Z is absent (so that the two bonds binding Z form a single bond, that is, -Z- is a bond) or is O—$CH_2$ or NH—$CH_2$ (with the O or N bound to the phenyl carrying (—R)$_n$, the $CH_2$ bound to the ring carrying (—R)$_m$, respectively);

T is $CH_2$ or preferably O or NQ, wherein Q is hydrogen, $C_1$-$C_7$-alkyl, $C_3$-$C_{10}$-cycloalkyl, $C_3$-$C_{10}$-cycloalkyl, phenyl or naphthyl-$C_1$-$C_7$-alkyl;

at least one of Ra and Rb is amino, amino-$C_1$-$C_7$-alkyl, such as aminomethyl or aminoethyl, hydrazino, amidino, amidino-$C_1$-$C_7$-alkyl, such as amidinomethyl or amidinoethyl, guanidino or guanidino-$C_1$-$C_7$-alkyl, such as guanidinomethyl or guanidinoethyl, where in each amino, hydrazino, amidino or guanidino mentioned each imino and/or each amino group present is, independently of the others, unsubstituted or substituted by one or in the case of amino two moieties independently selected from the group consisting of $C_1$-$C_7$-alkyl, phenyl, naphthyl, phenyl- or naphthyl-$C_1$-$C_7$-alkyl, $C_3$-$C_{10}$-cycloalkyl and $C_3$-$C_{10}$-cycloalkyl, while the other is also one of these moieties or is hydrogen or R;

each R if present (that is if n and/or m are 1 to 4, respectively or X is CR) is, independently of the others, replacing a hydrogen in the corresponding ring in formula I and is selected from the group consisting of $C_1$-$C_7$-alkyl, $C_1$-$C_7$-alkoxy-$C_1$-$C_7$-alkyl, halo-$C_1$-$C_7$-alkyl, phenyl- or naphthyl-$C_1$-$C_7$-alkyl, phenyl, naphthyl, halo, hydroxy, $C_1$-$C_7$-alkyloxy, phenyl- or naphthyl-$C_1$-$C_7$-alkyloxy, phenoxy, naphthoxy, $C_1$-$C_7$-alkanoyloxy, halo-$C_2$-$C_7$-alkanoyloxy, benzoyloxy, naphthyloxy, amino that is unsubstituted or substituted by one or two moieties independently selected from the group consisting of $C_1$-$C_7$-alkyl, phenyl-$C_1$-$C_7$-alkyl, naphthyl-$C_1$-$C_7$-alkyl, $C_1$-$C_7$-alkanoyl, benzoyl, naphthoyl, $C_3$-$C_{10}$-cycloalkyl and $C_3$-$C_{10}$-cycloalkyl, carboxy, $C_1$-$C_7$-alkoxycarbonyl, phenyl-$C_1$-$C_7$-alkoxycarbonyl, naphthyl-$C_1$-$C_7$-alkoxycarbonyl, $C_3$-$C_{10}$-cycloalkoxycarbonyl, $C_3$-$C_{10}$-cycloalkoxycarbonyl, carbamoyl, N-mono- or N,N-di-($C_1$-$C_7$-alkyl, phenyl-$C_1$-$C_7$-alkyl, naphthyl-$C_1$-$C_7$-alkyl, $C_1$-$C_7$-alkanoyl, benzoyl, naphthoyl, $C_3$-$C_{10}$-cycloalkyl and/or $C_3$-$C_{10}$-cycloalkyl)carbamoyl, sulfamoyl, N-mono- or N,N-di-($C_1$-$C_7$-alkyl, phenyl-$C_1$-$C_7$-alkyl, naphthyl-$C_1$-$C_7$-alkyl, $C_3$-$C_{10}$-cycloalkyl and/or $C_3$-$C_{10}$-cycloalkyl)sulfamoyl, nitro and cyano;

n is 0 to 4; and m is 0 to 4;

or a (preferably pharmaceutically acceptable) salt thereof.

The invention also relates to a compound of the formula I as defined above or below for use in the diagnostic or therapeutic treatment of a warm-blooded animal or a human, especially of a disease or disorder which depends on, more specifically which responds to modulation, especially inhibition, of a cysteine protease, especially UCH-L3 and/or USP2 and/or one or more altered or mutated forms of any one or more of these.

Another embodiment of the invention relates to a pharmaceutical formulation comprising a compound of the formula I as defined above or below, or a pharmaceutically acceptable salt thereof, an at least one pharmaceutically acceptable carrier material.

Yet another embodiment of the invention relates to the use of a compound of the formula I, or a pharmaceutically acceptable salt thereof, in the preparation of a pharmaceutical formulation for the treatment of a disease or disorder that depends on (especially inappropriate activity on a cysteine protease, especially one or more selected from the group consisting of UCH-L3 and/or USP2, and/or one or more altered or mutated forms of any one or more of these; or the use of said compounds in the treatment of a disease that depends on (especially inappropriate activity of) a cysteine protease, especially one or more selected from the group consisting of UCH-L3 and/or USP2, and/or one or more altered or mutated forms of any one or more of these.

The present invention also relates to a method of treating a cysteine protease, especially depends on (especially inappropriate activity of) a cysteine protease, especially UCH-L3 and/or USP2, dependent and/or proliferative disease comprising administering a compound of the formula I, or a pharmaceutically acceptable salt thereof, to a warm-blooded animal, especially a human.

Further embodiments of the invention can be found in the subsequent disclosure.

Listed below are definitions of various terms used to describe the compounds of the present invention as well as their use and synthesis, starting materials and intermediates and the like. These definitions, either by replacing one, more than one or all general expressions or symbols used in the present disclosure and thus yielding preferred embodiments of the invention, preferably apply to the terms as they are used throughout the specification unless they are otherwise limited in specific instances either individually or as part of a larger group. In other terms: Independently of each other, one or more of the more general expressions may be replaced by the more specific definitions, thus leading to preferred embodiments of the invention.

The term "lower" or "$C_1$-$C_7$-" defines a moiety with up to and including maximally 7, especially up to and including maximally 4, carbon atoms, said moiety being branched (one or more times) or straight-chained and bound via a terminal or a non-terminal carbon. Lower or $C_1$-$C_7$-alkyl, for example, is n-pentyl, n-hexyl or n-heptyl or preferably $C_1$-$C_4$-alkyl, especially as methyl, ethyl, n-propyl, sec-propyl, n-butyl, isobutyl, sec-butyl or tert-butyl. Where a substituent is present (e.g. in $C_3$-$C_{10}$-cycloalkyl-$C_1$-$C_7$-alkyl, phenyl-$C_1$-$C_7$-alkyl or the like), this substituent may be bound to any of the chain carbons, more preferably at a terminal ("ω"-) carbon.

Halo or halogen is preferably fluoro, chloro, bromo or iodo, most preferably fluoro, chloro or bromo, if not defined otherwise.

$C_3$-$C_{10}$-cycloalkyl is preferably $C_3$-$C_8$-cycloalkyl, such as cyclopropyl, cyclobutyl, cyclopentyl or cyclohexyl.

T is preferably O or NH.

Halo-$C_1$-$C_7$-alkyl can be $C_1$-$C_7$- (or preferably $C_1$-$C_4$) alkyl with one or more, e.g. up to three, halo substituents, for example trifluoromethyl.

Halo-$C_2$-$C_7$-alkanoyloxy can be $C_2$-$C_7$- (or preferably $C_2$-$C_4$-) alkyl with one or more, e.g. up to three, halo substituents, for example trifluoroacetyl.

$C_1$-$C_7$-alkoxy is preferably $C_1$-$C_4$-alkoxy, such as methoxy or ethoxy.

m is preferably 0, 1 or 2, more preferably 0 (zero).

n is preferably 0, 1 or 2, more preferably 0 (zero).

Salts are especially the pharmaceutically acceptable salts of compounds of formula I. They can be formed where salt forming groups, such as basic or acidic groups, are present that can exist in dissociated form at least partially, e.g. in a pH range from 4 to 10 in aqueous environment, or can be isolated especially in solid form.

Such salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example formic acid, acetic acid, trifluoroacetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethane-sulfonic acid, ethane-1,2-disulfonic acid, benzenesulfonic acid, 2-naphthalenesulfonic acid, 1,5-naphthalene-disulfonic acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, a compound of formula I may also form internal salts.

For isolation or purification purposes it is also possible to use pharmaceutically unacceptable salts, for example picrates or perchlorates. For therapeutic use, only pharmaceutically acceptable salts or free compounds are employed (where applicable comprised in pharmaceutical preparations), and these are therefore preferred.

In view of the close relationship between the compounds in free form and in the form of their salts, including those salts that can be used as intermediates, for example in the purification or identification of the compounds or salts thereof, any reference to "compounds" (including also starting materials and "intermediates") hereinbefore and hereinafter, especially to the compound(s) of the formula I, is to be understood as referring also to one or more salts thereof or a mixture of the free compound and one or more salts thereof, each of which is intended to include also any solvate, metabolic precursor such as ester or amide of the compound especially of formula I, or salt of any one or more of these, as appropriate and expedient and if not explicitly mentioned otherwise. Different crystal forms and solvates may be obtainable and then are also included, especially in the case of a compound of the formula I.

Where the plural form is used for compounds, salts, pharmaceutical preparations, diseases, disorders and the like, this is intended to mean also a single compound, salt, pharmaceutical preparation, disease or the like, where "a" or "an" is used, this means to refer to the indefinite article or preferably to "one".

In some cases, a compound of the present invention may comprise one or more chiral centers in substitutents or show other asymmetry (leading to enantiomers) or may otherwise be able to exist in the form of more than one stereoisomer, e.g. due more than one chiral centers or more than one other type of asymmetry or due to rings or double bonds that allow for Z/E (or cis-trans) isomerism (diastereomers). The present inventions includes both mixtures of two or more such isomers, such as mixtures of enantiomers, especially racemates, as well as preferably purified isomers, especially purified enantiomers or enantiomerically enriched mixtures.

As stated above, the compounds of the formula I have valuable pharmacological properties. Especially, they are useful in the treatment of (one or more) diseases that depend on (one or more) cysteine proteases, especially UCH-L3 and/or USP2.

The terms "treatment" or "therapy" (especially of cysteine protease, which preferably means UCH-L3 and/or USP2 wherever mentioned herein, dependent diseases or disorders) refer to the prophylactic (including preventative, e.g. in patients where mutations or changes have been found that indicate that they are or may be prone to the development of a disease) or preferably therapeutic (including but not limited to palliative, curative, symptom-alleviating, symptom-reducing, disease- or symptom-suppressing, progression-delaying, cysteine protease-regulating and/or cysteine protease-inhibiting) treatment of said diseases, especially of any one or more of the diseases mentioned below.

The term "curative" as used herein means efficacy in treating ongoing episodes involving (especially deregulated) cysteine protease activity.

The term "prophylactic" means the prevention of the onset or recurrence of diseases involving (especially deregulated) cysteine protease activity.

The term "delay of progression" as used herein especially means administration of the active compound to patients being in a pre-stage or in an early phase of the disease to be treated, in which patients for example a pre-form of the corresponding disease is diagnosed or which patients are in a condition, e.g. during a medical treatment or a condition resulting from an accident, under which it is likely that a corresponding disease will develop, or where e.g. metastasation can be expected without treatment.

A warm-blooded animal (or patient) is more preferably a mammal, especially a human.

Where subsequently or above the term "use" is mentioned (as verb or noun) (relating to the use of a compound of the formula I or a pharmaceutically acceptable salt thereof), this (if not indicated differently or suggested differently by the context) includes any one or more of the following embodiments of the invention, respectively (if not stated otherwise): the use in the treatment of an (especially deregulated) cysteine protease, such as UCH-L3 and/or USP2, activity dependent disease, the use for the manufacture of pharmaceutical compositions for use in the treatment of an (especially deregulated) cysteine protease, such as UCH-L3 and/or USP2, dependent disease, methods of use of one or more compounds of the formula I in the treatment of an (especially deregulated) cysteine protease, such as UCH-L3 and/or USP2, dependent and/or proliferative disease, pharmaceutical preparations comprising one or more compounds of the formula I for the treatment of said an (especially deregulated) cysteine protease, such as UCH-L3 and/or USP2, dependent disease, and one or more compounds of the formula I in the treatment of said an (especially deregulated) cysteine protease, such as UCH-L3 and/or USP2, dependent disease, as appropriate and expedient, if not stated otherwise. In particular, diseases to be treated and are thus preferred for "use" of a compound of formula I are selected from an (especially deregulated) cysteine protease, such as UCH-L3 and/or USP2, dependent (here as at all other places where used herein "dependent" meaning also "supported", not only "solely dependent", including also situations where a disease is responding to modulation, especially inhibition, of a cysteine protease, especially UCH-L3 and/or USP2) diseases mentioned below, especially proliferative diseases mentioned below.

Where a cysteine protease is mentioned, this relates to any type, including one or more altered or mutated or allelic forms of any one or more of these (e.g. those that result in conversion of a respective proto-oncogene into an oncogene, such as constitutively activated mutants). Especially an abnormally highly-expressed, constitutively activated or normal but in the given context of other regulatory mechanism in a patient relatively overactive, and/or mutated form is encompassed. For example, wherever UCH-L3 and/or USP2 are mentioned, this, also if not explicitly mentioned, may comprise the normal natural as well as one or more altered or mutated forms of any one or more of these enzymes.

The usefulness of the compounds of the present invention in the modulation, especially as inhibitors, of cysteine proteases can especially and paradigmatically be demonstrated by the following test systems:

Recombinant Expression and Purification of UCH-L3 and USP-2

UCH-L3 is expressed in *E. coli* in soluble form. The use of the GST-tag in the first purification step leads to fast and convenient purification. However, extended exposure of the protease with the GSH containing elution buffer has to be avoided due to the inactivation of the active side cysteine by GSH. After this purification step, the GST-tag is removed by using the engineered thrombin cleavage side between the tag and the mature protein. The final purification step (gel filtration) yields >95% pure protein as judged by SDS polyacrylamide gel electrophoresis. The fractions containing UCH-L3 activity are pooled and the solution is stored frozen at −80° C. In detail, the expression plasmid for UCH-L3 (which is subcloned from the library plasmid with GenBank N27190 by Polymerase Chain Reaction onto the EcoRI/XhoI sites of pGEX-4T1 (Amersham) encoding for a GST-UCH-L3 fusion protein) is transformed into *E. coli* strain BL21 (DE3)pLysS which is cultivated in LB medium containing 100 µg/ml ampicillin and 34 µg/ml chloramphenicol and induced at $OD_{600}$ of 0.5 with 0.5 mM IPTG. After 5 h of induction the cells are harvested by centrifugation. All purification steps are done at 4° C., unless stated otherwise. Cells from 4-L *E. coli* cell culture are resuspended in PBS buffer at pH 7.3 containing 1% (w/v) PMSF and 2 mM DTE and ruptured by sonication (4×30 s at 60% amplitude; Branson Digital Sonifier W-450D). After centrifugation of the homogenate at 75,000 g for 15 min, the supernatant is applied to a glutathione-Sepharose column (GSTPrep® FF 16/10; Amersham) equilibrated with PBS at a flow rate of 2 ml/min. After washing with three column volumes, UCH-L3 is eluted at a flow rate of 3 ml/min with PBS supplemented with 10 mM GSH. Fractions are analyzed by SDS-PAGE (4-20%) and the UCH-L3-containing fractions are pooled and concentrated to about 10 ml. Immediately after concentration, the sample is applied to a size-exclusion chromatography column (Superdex 75®, HiLoad® 26/60; Amersham) equilibrated with PBS to avoid extended exposure of GSH to the protein. The GST-fusion tag is removed by incubating the sample for 1 week with thrombin (10 U/mg protein) at 10° C. After the incubation, the sample is applied to a glutathione-Sepharose column (GST-Prep FF 16/10; Amersham) to remove the remaining undigested fusion protein. The flow-through containing thrombin and mature UCH-L3 is applied to a size-exclusion chromatography column (Superdex 75®), HiLoad® 26/60; Amersham) equilibrated with buffer C (10 mM Tris, 100 mM NaCl, pH 8.0) at a flow rate of 2.5 ml/min. The UCH-L3-containing fractions are pooled, dropped into liquid nitrogen, and stored at −80° C.

*E. coli* strain BL21(DE3)pLysS harboring the human USP2 expression plasmid (FSMB00224 human USP2 gene inserted in pET24; construct number: PIMB-0219_pET24a-hu USP-2 short-ST; Plasnova entry: NPL005152; Protrack Unique ID PP03-003234) is cultivated in LB medium containing 30 µg/ml kanamycin and induced at $OD_{600}$ of 0.5 with 0.5 mM IPTG. After 5 hours of induction the cells are harvested by centrifugation. All purification steps are done at 4° C., unless stated otherwise. Cells from 4 liter *E. coli* cell culture are resuspended in 50 mM Tris/HCl buffer at pH 8.0 and ruptured by sonication (4 times 30 seconds at 60% amplitude; Branson Digital Sonifier W450D). After centrifugation of the homogenate at 16500 g for 15 min, the supernatant is applied to a Strep-Tactin® column (16/10, IBA, Goettingen, Germany) equilibrated with buffer A (10 mM Tris/HCL, 100 mM NaCl, pH 8.0) at a flow rate of 2 ml/min. After washing with 3 column volumes, USP2 is eluted at a flow rate of 3 ml/min with buffer B (buffer A supplemented with 2.5 mM desthiobiotin pH 8.0). Fractions are analyzed by SDS-PAGE (4-20%) and the USP2 containing fractions are pooled and concentrated to about 5 ml. The sample is applied to a size exclusion chromatography column (Superdex® 75, HiLoad® 26/60, Amersham) equilibrated with buffer A at a flow rate of 2.5 ml/min. The USP2 containing fractions are pooled, dropped into liquid nitrogen and stored at −80° C.

| Fluorescence Polarization Assay Materials | |
|---|---|
| Assay buffer: | 75 mM Tris/HCl pH 7.5, 150 mM NaCl, 0.05% (w/v) CHAPS, 5 mM DTE, 1.5 mM EDTA |
| Substrate: | Ubiquitin-TAMRA (Stock solution 12.5 µM) |
| Compound: | Stock solution 100 mM in DMSO |
| Enzyme: | human recombinant UCH-L3 (Stock solution 70 uM) human recombinant USP2 catalytic domain (Stock solution 14.6 uM) |
| Filter set: | 535/595, TAMRA dichro (TECAN) |
| Plate: | Labsystems Microtiter, 384-well |

Methods

Human UCH-L3 (12 pM) or USP2 (4 nM) is pre-incubated in the absence or presence of increasing concentrations of test compounds of the formula I ranging for 1 nM to 100 µM (⅓ dilution) for 4 h at RT in a total volume of 20 µl assay buffer. The enzyme reaction is started by adding the substrate (10 µl) reaching a final concentration of 40 nM. Substrate hydrolysis is monitored using a fluorescence polarisation reading system (Fluoroskan Ascent) set to 535 nm for excitation and 595 nm for emission. Fluorescence polarisation readings are collected every 30 sec (up to 136 min). The effect of compound on the enzymatic activity is obtained from the linear time course. The apparent inhibition constant, $IC_{50}$, is calculated from the plot of percentage of inhibition versus inhibitor concentration using non-linear regression analysis software (XLfit, Vers 2.0.9; ID Business Solution Ltd., Guildford, Surrey, UK).

Determination of $K_M$, $k_{cat}$, and $k_{cat}/K_M$ for the Ubiquitin-TAMRA Substrate The $K_M$ value is obtained from measurements conducted at constant enzyme concentration (5 pM-UCH-L3 and 2 nM-USP-2) and different substrate concentrations (0, 10, 20, 40, 80, 150, 250, 500, 750, 1000 nM). Under conditions where the substrate concentration, [S], is significantly higher than the enzyme concentration, the enzymatic velocity, v, follows the Michaelis-Menten equation $$v=(v_{max}*[S])/([S]+K_M),\qquad\text{eq. 1}$$

where $v_{max}$ is the maximal velocity at saturating substrate concentrations.

Equation 1 can be applied to the curve obtained by plotting the measured enzyme velocities versus the corresponding substrate concentration leading to the values for $K_M$ and $v_{max}$ by a non-linear regression fit.

The $k_{cat}$ value is then defined as $$k_{cat} = v_{max}/[E_o],\qquad \text{eq. 2}$$

where $[E_o]$ is the total enzyme concentration.

|        | $K_M$ (nM) | $k_{cat}$ (M$^{-1}$s$^{-1}$) |
|--------|------------|------------------------------|
| USP-2  | 1800       | $2.3 \times 10^5$            |
| UCH-L3 | 106        | $7.2 \times 10^7$            |

Abbreviations used stand for:

LB medium: Luria-Bertani Medium; IPTG=isopropyl-β-galactopyranoside; Strep-Tactin®=engineered streptavidin that binds the Strep-tag II; CHAPS=3-[(3-chloramidopropyl) dimethylammonio)-propane sulfonic acid; DTE=dithiothreitol; TAMRA=tetramethylrhodamine; PMSF—phenylmethylsulfonylfluoride; PBS—phosphate buffered saline; DMSO—dimethylsulfoxide.

In these test systems, compounds of the formula I preferably show apparent inhibition constants, IC$_{50}$, in the range from 100 nM to 50 μM, more preferably from 100 nM to 10 μM, for inhibition of UCH-L3, and/or from 100 nM to 100 μM, more preferably from 100 nM to 50 μM, for inhibition of USP2.

The efficiency of compounds of the formula I as inhibitors of tumor growth can be demonstrated using various in vivo models. With such types of model, it is possible to show inhibition of tumor growth with compounds of the formula I if tested.

In view of their cysteine protease modulating (especially inhibiting) properties and/or possibly other not yet known mechanisms, the use of the present compounds in the treatment of a variety of proliferative diseases, including those mentioned below, and/or diseases that depend on (especially inappropriate) cysteine protease activity is possible.

For example, compounds of the present invention can be used in the treatment of different (especially primary, but also derived) solid tumors (including benign or especially malign types) such as sarcoma (e.g. Ewing sarcoma, Kaposi's sarcoma or soft part sarcomas such as Dermatofibrosarcoma protuberans), gastrointestinal stromal tumors (GIST), seminoma, carcinoids, mast cell tumors, lung carcinomas, such as small or large cell lung carcinoma, bronchial carcinomas, such as small cell bronchial carcinoma, seminomas, dysgerminomas, testicular intraepithelial neoplasias, melanomas, mamma carcinomas, neuroblastomas, papillary/follicular thyroid carcinoma, malign lymphomas, Non Hodgkin's lymphoma, multiple endocrine neoplasia type 2 (MEN 2), pheochromocytoma, thyroid carcinoma, e.g. medullary thyroid carcinoma, parathyroid hyperplasia/adenoma, mamma carcinoma, colon cancer, colorectal adenoma, ovarian cancer, prostate carcinoma, glioblastoma, brain tumors, prostate carcinoma (also including adenocarcinomas and bone metastasis), malign gliomes (anaplastic astrocytomas/glioblastomas), pancreatic cancer, malignant pleural mesothelioma, haemangioblastoma, haemangioma, carcinoma of the kidney, liver, adrenal gland, bladder, stomach (especially gastric tumors), rectum, vagina, cervix, endometrium, multiple myeloma, tumors of the neck and head, e.g. squamous carcinoma of the head and neck, including neoplasias, especially of epithelial character, e.g. in the case of mammary carcinoma, malignant nephrosclerosis; or further of other hyperplasias or proliferative diseases In addition, they can be useful as immunosuppressants, as an aid in scar-free wound healing, and for treating age spots and contact dermatitis.

Process of Manufacture

A compound of formula I can be prepared analogously to methods that, for other compounds, are in principle known in the art, so that for the novel compounds of the formula I the process is novel as analogy process, preferably by reacting a compound of the formula II,

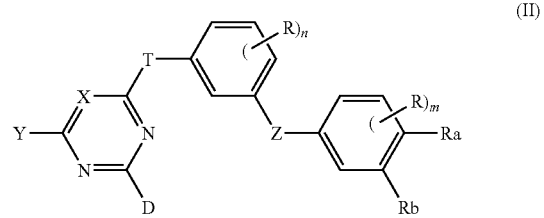

wherein D is a leaving group and X, A, Z, T, T, Ra, Rb, m and n have the meanings given for a compound of the formula I in claim 1, with a cyanide introducing reagent, and, if desired, transforming an obtainable compound of formula I into a different compound of formula I, transforming a salt of an obtainable compound of formula I into the free compound or a different salt, transforming an obtainable free compound of formula I into a salt thereof, and/or separating an obtainable mixture of isomers of a compound of formula I into individual isomers;

where in any starting material of the formula II functional groups that shall not take part in the manufacturing and/or a conversion reaction may be present in protected form and protecting groups are removed to obtain a compound of the formula I.

A leaving group D in a compound of the formula II is preferably halo, more preferably chloro. A cyanide introducing reagent is preferably a metal cyanide, for example an alkali metal cyanide, such as sodium or potassium cyanide. The reaction preferably takes place in the presence of a catalyst, such as 1,4-diazabicyclo[2.2.2]octane (DABCO).

The reaction preferably takes place in a solvent or solvent mixture, e.g. in water and/or dimethylsulfoxide, for example at temperatures in the range from 0 to 50° C., e.g. at lower temperatures in the range from 0 to 25° C.

Where a protecting group is present in a resulting protected compound of the formula I, this protecting group is subsequently removed, e.g. according to procedures known in the art and described, for example, in the standard textbooks mentioned below under "General Process Conditions". For example, tert-butoxycarbonyl as amino or imino protecting group can be removed by treatment with an acid, such as formic acid or trifluoroacetic acid, for example at temperatures in the range from 0 to 50° C., e.g. at 0 to 25° C.

Optional Reactions and Conversions

Compounds of the formula I, or protected forms thereof directly obtained according to the preceding procedure or after introducing protecting groups anew, which are included subsequently as starting materials for conversions as well even if not mentioned specifically, can be converted into different compounds of the formula I according to known procedures, where required followed removal of protecting groups.

For example, in a compound of the formula I (in free or protected form) wherein a nitrogen is present with a hydrogen atom, e.g. in the case of T=NH, Y is amino or Ra or Rb is or comprises amino or imino, the corresponding substitutents mentioned above or below can be introduced by reaction with the corresponding halides, e.g. iodides, bromides or chlorides, under customary reaction conditions.

Carboxy groups, e.g. R in formula I, can be converted into the corresponding $C_1$-$C_7$-alkoxycarbonyl of phenyl-$C_1$-$C_7$-alkoxycarbonyl groups by reaction with the corresponding alcohols under customary condensation or esterification conditions.

A salt of a compound of the formula I can be converted in customary manner into the free compound; metal and ammonium salts can be converted, for example, by treatment with suitable acids, and acid addition salts, for example, by treatment with a suitable basic agent. In both cases, suitable ion exchangers may be used.

Stereoisomeric mixtures, e.g. mixtures of diastereomers, can be separated into their corresponding isomers in a manner known per se by means of appropriate separation methods. Diastereomeric mixtures for example may be separated into their individual diastereomers by means of fractionated crystallization, chromatography, solvent distribution, and similar procedures. This separation may take place either at the level of one of the starting compounds or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

Intermediates and final products can be worked up and/or purified according to standard methods, e.g. using chromatographic methods, distribution methods, (re-) crystallization, and the like.

Starting Materials

Starting Materials, including intermediates, for compounds of the formula I, such as the compounds of the formula II, can be prepared, for example, according to methods that are known in the art, according to methods described in the examples or methods analogous to those described in the examples, and/or they are known or commercially available.

In the subsequent description of starting materials and intermediates and their synthesis, X, A, Z, T, T, Ra, Rb, m and n have the meanings given above for compounds of the formula I or in the Examples for the respective starting materials or intermediates, if not indicated otherwise directly or by the context. Protecting groups, if not specifically mentioned, can be introduced and removed at appropriate steps in order to prevent functional groups, the reaction of which is not desired in the corresponding reaction step or steps, employing protecting groups, methods for their introduction and their removal are as described above or below, e.g. in the references mentioned under "General Process Conditions". The person skilled in the art will readily be able to decide whether and which protecting groups are useful or required.

A starting material of the formula II wherein Z is O—$CH_2$ or NH—$CH_2$ (and the other symbols have the meanings indicated for a compound of the formula II) may be prepared, for example, by reacting a hydroxy compound of the formula III,

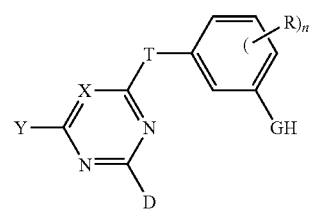

wherein G is O or NH and D and the other symbols are as defined for a compound of the formula II, with a compound of the formula IV,

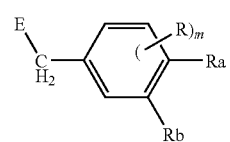

wherein E is a nucleofugal group and the other symbols are as defined for a compound of the formula II. The reaction preferably takes place in the presence of a base, especially an alkali metal carbonate, more especially caesium carbonate, especially of G is O, or a nitrogen base, e.g. a tertiary nitrogen base, such as triethylamine, e.g. if G is NH. A nucleofugal group E is preferably halo, such as chloro, bromo or iodo. The reaction preferably takes place in an appropriate solvent or solvent mixture, e.g. in N,N-dimethylformamide, and a quaternary ammonium salt, e.g. tetrabutylammonium iodide, and the temperatures can, for example, be in the range from 0 to 50° C., e.g. about at room temperature.

A compound of the formula III wherein T is O or NQ can, for example, be prepared by reacting a compound of the formula V,

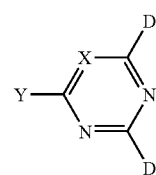

wherein D is as defined for (where the two D need not be identical) is a leaving group and is, as well as the other symbols, as defined for a compound of the formula II, with a compound of the formula VI,

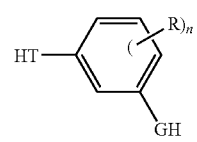

wherein T is NQ or O, in the presence of a base, e.g. an alkali metal hydroxide, such as sodium hydroxide, in an appropriate solvent or solvent mixture, e.g. water and/or acetone, at temperatures e.g. from −10 to 50° C., e.g. from 0 to 25° C.

A starting material of the formula II, wherein Z is absent (that is, a biphenyl compound of the formula II wherein -Z- is a bond) and T is O or NQ and the other symbols are as defined for a compound of the formula II can, for example, be prepared by reacting a compound of the formula V, as given and defined above, with a compound of the formula VII,

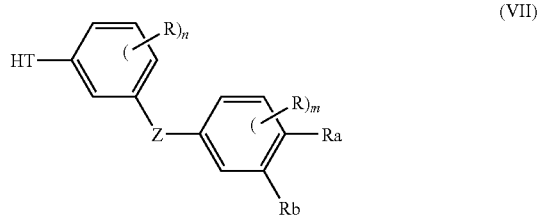

wherein T is O or NQ, Z is absent (meaning -Z- is a bond) and the other symbols are as defined for a compound of the formula I or II, in the presence of a base, e.g. an alkali metal carbonate, such as potassium or sodium carbonate, preferably in an appropriate solvent or solvent mixture, such as N,N-dimethylformamide and/or acetonitrile, for example at temperatures in the range from −10 to 50° C., e.g. from 0 to 25° C.

A compound of the formula VII can, for example, be prepared by reacting a boronic acid of the formula VIII,

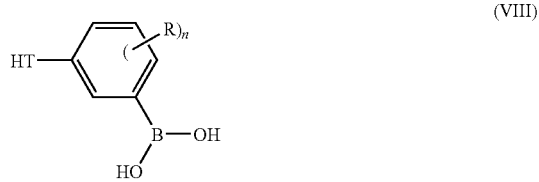

wherein T is and the other symbols are as defined for a compound of the formula II or I, with a compound of the formula IX,

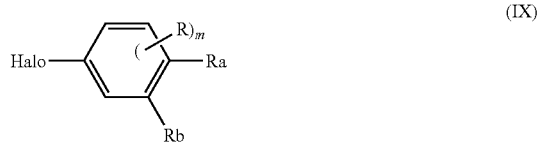

wherein halo is halogen, e.g. chloro or bromo, and the other symbols are as defined for a compound of the formula II or I, in the presence of a base, e.g. an alkali metal carbonate, such as sodium carbonate, and a catalyst, e.g. palladium(II)acetate, and of tri-cyclohexylphosphine in an appropriate solvent or solvent mixture, e.g. water and/or dioxane, at elevated temperatures, e.g. from 50° C. to the boiling temperature of the reaction mixture, for example from 90 to 100° C. (for example under microwave heating).

A compound of the formula II wherein Ra and/or Rb, especially Ra or Rb is amidino can be prepared from an analogue of a compound of the formula II wherein instead of Ra and Rb other than hydrogen or R as defined for a compound of the formula I a cyano group is pre-sent at the position of Ra and/or Rb, especially Ra or Rb. The conversion of a cyano group to an amidino group can take under customary conditions, especially by first forming the corresponding imido ester in the presence of an alcohol, such as a hydroxy-$C_1$-$C_7$-alkane, e.g. ethanol, in the absence or presence of a further solvent, such as dichloromethane or chloroform, in the presence of an acid, e.g. hydrogen chloride, for example at temperatures from −10 to 50° C., e.g. 0 to 5° C., and subsequently (with or without isolation of the resulting imido ester with ammonia or N-mono- or N,N-di-($C_1$-$C_7$-alkyl, phenyl, naphthyl, phenyl- or naphthyl-$C_1$-$C_7$-alkyl, $C_3$-$C_{10}$-cycloalkyl and/or $C_3$-$C_{10}$-cycloalkyl) -amine (preferably in the presence of a corresponding ammonium salt, e.g. a halogenide, such as chloride) in an appropriate solvent, such as an alcohol, e.g. methanol at temperatures in the range from, for example, −10 to 50° C., e.g. from 0 to 25° C. to the corresponding amidino compound of the formula II wherein Ra and/or Rb is amidino or N-mono- or N,N-di-($C_1$-$C_7$-alkyl, phenyl, naphthyl, phenyl- or naphthyl-$C_1$-$C_7$-alkyl, $C_3$-$C_{10}$-cycloalkyl and/or $C_3$-$C_{10}$-cycloalkyl)-amidino.

Any of the starting materials of the formula II, III, IV, V, VI, VII, VIII or IX may, where desired or required, carry protection groups at functional groups that are not intended to take part in the respective reactions of the compounds of these formulae, which can be removed from the final product of the formula I and/or at any other appropriate intermediate stage. The introduction and removal of protecting groups, such as tert-butoxycarbonyl for amino groups to be protected, also takes place under customary conditions, e.g. as described in the standard textbooks cited under "General Process Conditions", and the protecting groups described therein can be used as appropriate. For example, the introduction of a tert-butoxycarbonyl amino protecting group can take place with tert-butoxycarbonic anhydride in the presence of a base, such as sodium carbonate, in an appropriate solvent or solvent mixture, e.g. tetrahydrofurane and/or water, e.g. at temperatures from 0 to 50° C.

Other starting materials, e.g. those of the formula II or III wherein T is $CH_2$, of the formula V, of the formula VI, of the formula VIII, of the formula IX and others, are known in the art, commercially available and/or can be prepared according to known or standard procedures, e.g. in analogy to or by methods described in the Examples.

General Process Conditions

The following applies in general to all processes mentioned hereinbefore and hereinafter, while reaction conditions specifically mentioned above or below are preferred:

In any of the reactions mentioned hereinbefore and hereinafter, protecting groups may be used where appropriate or desired, even if this is not mentioned specifically, to protect functional groups that are not intended to take part in a given reaction, and they can be introduced and/or removed at appropriate or desired stages. Reactions comprising the use of protecting groups are therefore included as possible wherever reactions without specific mentioning of protection and/or deprotection are described in this specification.

Within the scope of this disclosure only a readily removable group that is not a constituent of the particular desired end product of formula I is designated a "protecting group", unless the context indicates otherwise. The protection of functional groups by such protecting groups, the protecting groups themselves, and the reactions appropriate for their removal are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosäuren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide und Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

All the above-mentioned process steps can be carried out under reaction conditions that are known per se, preferably those mentioned specifically, in the absence or, customarily, in the presence of solvents or diluents, preferably solvents or diluents that are inert towards the reagents used and dissolve them, in the absence or presence of catalysts, condensation or neutralizing agents, for example ion exchangers, such as cation exchangers, e.g. in the H$^+$ form, depending on the nature of the reaction and/or of the reactants at reduced, normal or elevated temperature, for example in a temperature range of from about −100° C. to about 190° C., preferably from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, e.g. as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of these, for example aqueous solutions, unless otherwise indicated in the description of the processes. Such solvent mixtures may also be used in working up, for example by chromatography or partitioning.

Intermediates and final products can be worked up and/or purified according to standard methods, e.g. using chromatographic methods, distribution methods, (re-) crystallization, distillation (under normal or reduced pressure), steam distillation and the like.

The invention relates also to those forms of the process in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention is produced under the process conditions and processed further in situ. In the process of the present invention those starting materials are preferably used which result in compounds of formula I described as being preferred. Special preference is given to reaction conditions that are identical or analogous to those mentioned in the Examples. The invention also relates to novel intermediates as well as salts thereof where salt-forming groups are present, as well as their synthesis.

PREFERRED EMBODIMENTS ACCORDING TO THE INVENTION

In the following preferred embodiments as well as in preceding and following embodiments of more general scope, any one or more or all general expressions can be replaced by the corresponding more specific definitions provided above and below, thus yielding stronger preferred embodiments of the invention.

The invention relates especially to a compound of the formula I wherein

X is CH, CR or N;

Y is hydrogen or $C_1$-$C_4$-alkyl, $C_3$-$C_8$-cycloalkyl, $C_1$-$C_4$-alkyloxy, $C_3$-$C_8$-cycloalkyloxy or amino that is unsubstituted or substituted by one or two moieties selected from the group consisting of $C_1$-$C_4$-alkyl and $C_3$-$C_8$-cycloalkyl;

Z is absent (so that the two bonds binding Z form a single bond) or is O—$CH_2$ or NH—$CH_2$;

T is $CH_2$, O or NQ, wherein Q is hydrogen, $C_1$-$C_4$-alkyl, $C_3$-$C_8$-cycloalkyl, $C_3$-$C_8$-cycloalkyl, phenyl or naphthyl-$C_1$-$C_4$-alkyl;

at least one of Ra and Rb is amino, amino-$C_1$-$C_4$-alkyl, such as aminomethyl or aminoethyl, hydrazino, amidino, amidino-$C_1$-$C_4$-alkyl, such as amidinomethyl or amidinoethyl, guanidino or guanidino-$C_1$-$C_4$-alkyl, such as guanidinomethyl or guanidinoethyl, where in each amino, hydrazino, amidino or guanidino;

each R if present (that is if n and/or m are 1 to 2, respectively or X is CR) is, independently of the others, replacing a hydrogen in the corresponding ring in formula I and is selected from the group consisting of $C_1$-$C_4$-alkyl, halo, hydroxy, $C_1$-$C_4$-alkyloxy, $C_2$-$C_4$-alkanoyloxy, amino that is unsubstituted or substituted by one or two moieties independently selected from the group consisting of $C_1$-$C_4$-alkyl, phenyl-$C_1$-$C_4$-alkyl, carboxy, $C_1$-$C_4$-alkoxycarbonyl, carbamoyl, sulfamoyl, nitro and cyano;

n is 0 to 2, preferably 0 or 1; and m is 0 to 2, preferably 0 or 1;

or a (preferably pharmaceutically acceptable) salt thereof.

The invention relates very especially to a compound of the formula I wherein

X is CH or N;

Y is hydrogen;

Z is absent (so that the two bonds binding Z form a single bond) or is O—$CH_2$;

T is O or NH;

Ra is aminomethyl, 2-aminoethyl, amidino or guanidino and Rb is hydrogen, or

Ra is hydrogen and Rb is aminomethyl, 2-aminoethyl, amidino or guanidino; and each of n and m is zero;

or a (preferably pharmaceutically acceptable) salt thereof.

Especially preferred are the compounds of the formula I, or the (especially pharmaceutically acceptable) salts thereof, novel starting materials and novel processes mentioned in the examples.

Pharmaceutical Compositions

The invention relates also to pharmaceutical compositions comprising a compound of formula I, to the use of a compound of the formula I in the therapeutic (in a broader aspect of the invention also prophylactic) treatment or a method of treatment of a disease or disorder that depends on (especially inappropriate) cysteine protease activity or responds to modulation, especially inhibition, of such a cysteine protease, especially the disorders or diseases mentioned as preferred above, to the compounds for said use and to pharmaceutical preparations and their manufacture, especially for said uses. More generally, pharmaceutical preparations are useful in case of compounds of the formula I, which may also be present in the form of their (especially pharmaceutically acceptable) salts, and are thus an embodiment of the invention.

The pharmacologically active compounds of the formula I may be present in or employed, for example, for the preparation of pharmaceutical compositions that comprise an effective amount of a compound of the formula I, or a pharmaceutically acceptable salt thereof, as active ingredient together or in admixture with one or more (e.g. inorganic or organic, solid or liquid) pharmaceutically acceptable carriers (carrier materials).

The invention relates also to a pharmaceutical composition that is suitable for administration to a warm-blooded animal, especially a human (or to cells or cell lines derived from a warm-blooded animal, especially a human, e.g. lymphocytes), for the treatment (this, in a broader aspect of the invention, also including prevention of (=prophylaxis against)) a disease that responds to modulation, especially inhibition of cysteine protease activity, comprising a compound of formula I or a pharmaceutically acceptable salt thereof, preferably in an amount which is effective against said disease, together with at least one pharmaceutically acceptable carrier.

The pharmaceutical compositions according to the invention are those for enteral, such as nasal, rectal or oral, or parenteral, such as intra-articular, subcutaneous, intramuscular or intravenous, administration to warm-blooded animals (especially a human), that comprise a pharmaceutically effective dose of the pharmacologically active ingredient, alone or together with a significant amount of a pharmaceutically acceptable carrier. The dose of the active ingredient depends on the species of warm-blooded animal, the body weight, the age and the individual condition, individual pharmacokinetic data, the disease to be treated and the mode of administration.

The invention relates also to method of treatment for a disease that responds to inhibition of a disease that depends on (especially inappropriate) activity of a cysteine protease; which comprises administering a prophylactically or especially therapeutically effective amount of a compound of formula I, or a pharmaceutically acceptable salt thereof, to an animal, especially to a warm-blooded animal, for example a human, that, on account of one or more of the mentioned diseases, is in need of such treatment.

The dose of a compound of the formula I or a pharmaceutically acceptable salt thereof to be administered to warm-blooded animals, for example humans of approximately 70 kg body weight, preferably is from approximately 3 mg to approximately 10 g, more preferably from approximately 10 mg to approximately 1.5 g, most preferably from about 100 mg to about 1000 mg/person/day, divided preferably into 1-3 single doses which may, for example, be of the same size. Usually, children receive half of the adult dose.

The pharmaceutical compositions comprise from approximately 1% to approximately 96%, preferably from approximately 20% to approximately 95%, active ingredient. Pharmaceutical compositions according to the invention may be, for example, in unit dosage form, such as in the form of ampoules, vials, suppositories, dragées, tablets or capsules.

The pharmaceutical compositions of the present invention are prepared in a manner known per se, for example by means of conventional dissolving, lyophilizing, mixing, granulating or confectioning processes.

Solutions of the active ingredient, and also suspensions, and especially isotonic aqueous solutions or suspensions, are preferably used, it being possible, for example in the case of lyophilized compositions that comprise the active ingredient alone or together with a carrier, for example mannitol, for such solutions or suspensions to be produced prior to use. The pharmaceutical compositions may be sterilized and/or may comprise excipients, for example preservatives, stabilizers, wetting and/or emulsifying agents, solubilizers, salts for regulating the osmotic pressure and/or buffers, and are prepared in a manner known per se, for example by means of conventional dissolving or lyophilizing processes. Said solutions or suspensions may comprise viscosity-increasing substances, such as sodium carboxymethylcellulose, carboxymethylcellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as the acid component a long-chained fatty acid having from 8-22, especially from 12-22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brasidic acid or linoleic acid, if desired with the addition of antioxidants, for example vitamin E, β-carotene or 3,5-di-tert-butyl-4-hydroxytoluene. The alcohol component of those fatty acid esters has a maximum of 6 carbon atoms and is a mono- or poly-hydroxy, for example a mono-, di- or tri-hydroxy, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Paris), "Miglyol 812" (triglyceride of saturated fatty acids with a chain length of C8 to C12, Hüls AG, Germany), but especially vegetable oils, such as cottonseed oil, almond oil, olive oil, castor oil, sesame oil, soybean oil and groundnut oil.

The injection or infusion compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, dragée cores or capsules. It is also possible for them to be incorporated into plastics carriers that allow the active ingredients to diffuse or be released in measured amounts.

Suitable carriers are especially fillers, such as sugars, for example lactose, saccharose, mannitol or sorbitol, cellulose preparations and/or calcium phosphates, for example tricalcium phosphate or calcium hydrogen phosphate, and binders, such as starch pastes using for example corn, wheat, rice or potato starch, gelatin, tragacanth, methylcellulose, hydroxypropylmethylcellulose, sodium carboxymethylcellulose and/or polyvinylpyrrolidone, and/or, if desired, disintegrators, such as the above-mentioned starches, and/or carboxymethyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and soft sealed capsules made of gelatin and a plasticizer, such as glycerol or sorbitol. The dry-filled capsules may comprise the active ingredient in the form of granules, for example with fillers, such as lactose, binders, such as starches, and/or glidants, such as talc or magnesium stearate, and if desired with stabilizers. In soft capsules the active ingredient is preferably dissolved or suspended in suitable oily excipients, such as fatty oils, paraffin oil or liquid polyethylene glycols, it being possible also for stabilizers and/or antibacterial agents to be added. Dyes or pigments may be added to the tablets or dragée coatings or the capsule casings, for example for identification purposes or to indicate different doses of active ingredient.

A compound of the formula I may also be used to advantage in combination with other agents active against a disease to be treated, especially antiproliferative agents. Such antiproliferative agents include, but are not limited to aromatase inhibitors; antiestrogens; topoisomerase I inhibitors; topoisomerase II inhibitors; microtubule active agents; alkylating agents; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further antiangiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; agents used in the treatment of hematologic malignancies; compounds which target, decrease or inhibit the activity of Flt-3; Hsp90 inhibitors; and temozolomide (TEMODAL®).

The structure of the active agents which can be identified by code nos., generic or trade names may be taken from the actual edition of the standard compendium "The Merck Index" or from databases, e.g. Patents International (e.g. IMS World Publications).

The above-mentioned compounds, which can be used in combination with a compound of the formula I, can be prepared and administered as described in the art such as in the documents cited above.

A compound of the formula I may also be used to advantage in combination with known therapeutic processes, e.g., the administration of hormones, radiation and/or surgery.

By "combination", there is meant either a fixed combination in one dosage unit form, or a kit of parts for the combined administration where a compound of the formula I and a combination partner may be administered independently at the same time or separately within time intervals that especially allow that the combination partners show a cooperative, e.g. synergistic, effect, or by making use of administration schedules representing any combination thereof. For example, combinations may also be present in the form of a kit of parts, that is, a product that allows for the simultaneous, sequential and/or independent administration of at least one compound of the formula I and one or more other combinations partners, e.g. selected from the antiproliferative agents mentioned above.

EXAMPLES

The following examples serve to illustrate the invention without limiting the scope thereof.

Temperatures are measured in degrees Celsius. Unless otherwise indicated, the reactions take place at rt.

The following abbreviations are used:
AcOH acetic acid
aq. Aqueous
brine sodium chloride solution saturated at rt
DABCO 1,4-diazabicyclo-[2.2.2]-octane
DCM dichloromethane
DMF N,N-dimethylformamide
DMSO dimethylsulfoxide
d6-DMSO perdeuterated DMSO
ES electrospray
ESI electrospray ionisation
EtOAc ethyl acetate
h hour(s)
HPLC High Performance Liquid Chromatography
MeOH methanol
min minute(s)
MS Mass Spectrometry
NMR Nuclear Magnetic Resonance
Rf Ratio of fronts value
rt room temperature
TFA trifluoroacetate
$t_{Ret}$ retention time Where no temperature is mentioned, a reaction takes place at room temperature.

The following trademarks are used:
Nucleosil=Nucleosil®, trademark of Macherey & Nagel, Düren, Germany, for HPLC column fillings
EXTUBE=EXTUBE®, trademark of Varian, Inc., Palo Alto, Calif., for liquid-liquid extraction cartridges.
Lichroprep=LiChroprep®, Merck KGaA, Darmstadt, Germany, for chromatography column fillings Thin Layer Chromatography (TLC) conditions: The $R_f$ values which indicate the ratio of the distance moved by each substance to the distance moved by the eluent front are determined on silica gel thin-layer plates 5×10 cm TLC plates, silica gel $F_{254}$ (Merck, Darmstadt, Germany) by thin-layer chromatography using the solvent systems indicated below.

Analytical HPLC Conditions:

System 1

Linear gradient 20-100% $CH_3CN$ (0.1% TFA) and $H_2O$ (0.1% TFA) in 5 min, then 1.5 min 100% $CH_3CN$ (0.1% TFA); detection at 215 nm, flow rate 1 mL/min at 30° C. Column: Nucleosil 100-3 C18HD (70×4.0 mm)

Example 1

4-(4'-Aminomethyl-biphenyl-3-yloxy)-pyrimidine-2-carbonitrile, Salt with Formic Acid A solution of [3'-(2-cyano-pyrimidin-4-yloxy)-biphenyl-4-ylmethyl]-carbamic acid tert-butyl ester (10 mg) in formic acid (0.154 ml) is stirred at rt for 1 h. This solution is evaporated under reduced pressure. The remaining oil is treated with diethyl ether to obtain crystals of 4-(4'-aminomethyl-biphenyl-3-yloxy)-pyrimidine-2-carbonitrile as salt with formic acid.

MS (ESI+): 303 [M+Na]; Rf: (DCM/MeOH=9/1, 1% NH$_3$aq.): 0.45; 1H-NMR (400 MHz, d6-DMSO): delta=8.88 (d, 1H); 8.36 (s, 1H); 7.75-7.50 (m, 8H); 7.32 (d, 1H); 3.85 (s, 2H).

The starting materials are prepared as follows:

Stage 1.1: (3'-Hydroxy-biphenyl-4-ylmethyl)-carbamic acid tert-butyl ester

A mixture of (4-bromo-benzyl)-carbamic acid tert-butyl ester (600 mg), 3-hydroxybenzeneboronic acid (373 mg), sodium carbonate (333 mg), palladium (II) acetate (10 mg) and tricyclohexylphosphine (13 mg) in water (3.5 ml) and dioxane (14 ml) is kept at 90° C. under micro wave conditions for 230 min. The mixture is cooled down to rt and is filtered through an EXTUBE extraction column with EtOAc (200 ml). The filtrate is evaporated and the resulting crude product is purified on silica (90 g) with cyclohexane/EtOAc 95:5 to 70:30 to afford pure (3'-hydroxy-biphenyl-4-ylmethyl)-carbamic acid tert-butyl ester.

MS (ESI+): 322 [M+Na]; Rf: (EtOAc/hexane=1/2): 0.28.

Stage 1.2: [3'-(2-Chloro-pyrimidin-4-yloxy)-biphenyl-4-ylmethyl]-carbamic acid tert-butyl ester A mixture of (3'-hydroxy-biphenyl-4-ylmethyl)-carbamic acid tert-butyl ester (435 mg), 2,4-dichloropyrimidine (221 mg) and potassium carbonate (295 mg) in DMF (10 ml) is stirred at rt for 20 h. This mixture is quenched with brine and extracted twice with EtOAc. The combined organic phases are dried over sodium sulfate, the solvent is evaporated and the resulting crude product is purified on silica (90 g) with cyclohexane/EtOAc 80/20 to afford pure [3'-(2-chloro-pyrimidin-4-yloxy)-biphenyl-4-ylmethyl]-carbamic acid tert-butyl ester.

MS (ESI+): 434 [M+Na]; Rf: (EtOAc/hexane=1/2): 0.30.

Stage 1.3: [3'-(2-Cyano-pyrimidin-4-yloxy)-biphenyl-4-ylmethyl]-carbamic acid tert-butyl ester A mixture of [3'-(2-chloro-pyrimidin-4-yloxy)-biphenyl-4-ylmethyl]-carbamic acid tert-butyl ester (161 mg), potassium cyanide (76 mg) and 1,4-diazabicyclo[2,2,2]octane (13 mg) in water (0.4 ml) and DMSO (2 ml) is left at 5° C. for 4 h. This mixture is acidified with AcOH to pH 4-5, quenched with brine and extracted twice with diethyl ether. The combined organic phases are dried over sodium sulfate, the solvent is evaporated and the crude product is purified on silica (15 g) with cyclohexane/EtOAc=5/1 to afford pure [3'-(2-cyano-pyrimidin-4-yloxy)-biphenyl-4-ylmethyl]-carbamic acid tert-butyl ester.

MS (ESI+): 425 [M+Na]; Rf: (EtOAc/hexane=1/2): 0.27.

Example 2

4-(4'-Aminomethyl-biphenyl-3-ylamino)-[1,3,5]triazine-2-carbonitrile, Salt with Formic Acid A solution of [3'-(4-cyano-[1,3,5]triazin-2-ylamino)-biphenyl-4-ylmethyl]-carbamic acid tert-butyl ester (43 mg) in formic acid (1 ml) is stirred at 5° C. for 4.5 h. This solution is evaporated under reduced pressure. The remaining oil is treated with diethyl ether to obtain crystals of 4-(4'-aminomethyl-biphenyl-3-ylamino)-[1,3,5]triazine-2-carbonitrile, salt with formic acid.

MS (ESI+): 303 [M+H]; Rf: (DCM/MeOH=9/1, 1% NH3aq.): 0.33; 1H-NMR (300 MHz, d6-DMSO): delta=8.88 (s, 1H); 8.28 (s, 1H); 7.92 (s, br, 1H); 7.65-7.4 (m, 7H); 3.98 (s, 2H).

The starting materials are prepared as follows:

Stage 2.1: [3'-(4-Chloro-[1,3,5]triazin-2-ylamino)-biphenyl-4-ylmethyl]-carbamic acid tert-butyl ester A mixture of (3'-amino-biphenyl-4-ylmethyl)-carbamic acid tert-butyl ester (48 mg), 2,4-dichlorotriazine (20 mg) and sodium carbonate in acetonitrile (1.5 ml) is stirred at 0° C. for 7 h. This mixture is filtered and purified by preparative HPLC (gradient of water, 0.1% TFA/acetonitrile, 0.1% TFA from 80/20 to 0/100 on Nucleosil 100-10 C18 column). The fractions containing product are basified with sodium carbonate, evaporated and filtered through an EXTUBE extraction column with EtOAc (80 ml). The filtrate is evaporated to afford pure [3'-(4-chloro-[1,3,5]triazin-2-ylamino)-biphenyl-4-ylmethyl]-carbamic acid tert-butyl ester.

MS (ESI−): 410 (M−H); Rf: (EtOAc/hexane=1/2): 0.31.

Stage 2.2: [3'-(4-Cyano-[1,3,5]triazin-2-ylamino)-biphenyl-4-ylmethyl]-carbamic acid tert-butyl ester A mixture of [3'-(4-chloro-[1,3,5]triazin-2-ylamino)-biphenyl-4-ylmethyl]-carbamic acid tert-butyl ester (55 mg), potassium cyanide (22 mg) and 1,4-diazabicyclo[2,2,2]octane (4 mg) in water (0.3 ml) and DMSO (1.3 ml) is stirred at 5° C. for 1.5 h. This mixture is acidified with 3 drops of AcOH, quenched with brine and extracted three times with diethyl ether. The combined organic phases are dried over sodium sulfate, the solvent is evaporated and the crude product is purified on silica (4 g) with cyclohexane/EtOAc=4/1 to afford pure [3'-(4-cyano-[1,3,5]triazin-2-ylamino)-biphenyl-4-ylmethyl]-carbamic acid tert-butyl ester.

MS (ESI+): 425 [M+Na]; Rf: (EtOAc/hexane=1/2): 0.33.

Example 3

N-[3'-(2-Cyano-pyrimidin-4-yloxy)biphenyl-4-yl]-guanidine, Salt with Trifluoroacetic Acid A mixture of N-[3'-(2-chloro-pyrimidin-4-yloxy)biphenyl-4-yl]-guanidine (66 mg), potassium cyanide (35 mg) and 1,4-diazabicyclo[2,2,2]octane (6 mg) in water (0.2 ml) and DMSO (1 ml) is stirred at rt for 2.5 h. This mixture is acidified with trifluoroacetic acid to pH 4-5 and purified by preparative HPLC (gradient of water, 0.1% TFA/acetonitrile, 0.1% TFA from 80/20 to 0/100 on Nucleosil 100-10 C18 column). The fractions containing product are lyophilized giving the trifluoroacetate salt of N-[3'-(2-cyano-pyrimidin-4-yloxy)biphenyl-4-yl]-guanidine.

MS (ESI+): 331 [M+H]; Rf: (EtOAc/AcOH=10/1): 0.22.

Stage 3.1: N-(3'-hydroxy-biphenyl-4-yl)guanidine

A mixture of 4-chlorophenylguanidine carbonate (644 mg), 3-(4,4,5,5-tetramethyl-1,3,2-dioxaborolan-2-yl)phenol (373 mg), sodium carbonate (495 mg), palladium (II) acetate (14 mg) and tricyclohexylphosphine (19 mg) in water (1.2 ml) and dioxane (5.7 ml) is kept at 100° C. under micro wave conditions for 200 min. The mixture is cooled down to rt, basified with 1 N NaOH to pH 10.5 and extracted 4 times with EtOAc. The combined organic phases are washed with brine and dried over sodium sulfate. The solvent is evaporated to afford crude N-(3'-hydroxy-biphenyl-4-yl)guanidine.

MS (ESI+): 228 [M+H]

Stage 3.2: N-[3'-(2-Chloro-pyrimidin-4-yloxy)biphenyl-4-yl]-guanidine

A mixture of N-(3'-hydroxy-biphenyl-4-yl)guanidine (550 mg), 2,4-dichloropyrimidine (146 mg) and potassium carbonate (196 mg) in DMF (8 ml) is stirred at rt for 20 h. This mixture is purified by preparative HPLC (gradient of water, 0.1% TFA/acetonitrile, 0.1% TFA from 80/20 to 0/100 on Nucleosil 100-10 C18 column). The fractions containing product are basified with 1 N NaOH to pH 8, evaporated and dried under reduced pressure. The residue is stirred in ethanol, the solvent is evaporated and dried under reduced pressure to afford crude N-[3'-(2-chloro-pyrimidin-4-yloxy)biphenyl-4-yl]-guanidine.

MS (ESI+): 340 [M+H].

Example 4

[4-(4'-Aminoethyl-biphenyl-3-yloxy)-pyrimidine-2-carbonitrile, Salt with Formic Acid A solution of {2-[3'-(2-cyano-pyrimidin-4-yloxy)-biphenyl-4-yl]-ethyl}carbamic acid tert-butyl ester (38 mg) in formic acid (0.35 ml) is stirred at rt for 1 h. This solution is evaporated under reduced pressure. The remaining oil is treated with diethyl ether to obtain crystals of 4-(4'-aminoethyl-biphenyl-3-yloxy)-pyrimidine-2-carbonitrile as salt with formic acid.

MS (ESI+): 317 [M+Na]; Rf: (DCM/MeOH=9/1, 1% NH3aq.): 0.36; 1H-NMR (400 MHz, d6-DMSO): delta=8.88 (d, 1H); 8.36 (s, 1H); 7.70-7.30 (m, 9H); 3.06 (m, 2H); 2.92 (m, 2H).

The starting materials are prepared as follows:

Stage 4.1: [2-(3'-Hydroxy-biphenyl-4-yl)-ethyl]-carbamic acid tert-butyl ester

A mixture of [2-(4-bromo-phenyl)-ethyl]-carbamic acid tert-butyl ester (500 mg), 3-hydroxybenzeneboronic acid (296 mg), sodium carbonate (265 mg), palladium (II) acetate (7 mg) and tricyclohexylphosphine (10 mg) in water (3 ml) and dioxane (12 ml) is kept at 90° C. under micro wave conditions for 180 min. The mixture is cooled down to rt and is filtered through an EXTUBE extraction column (Varian) with EtOAc (200 ml). The filtrate is evaporated and the resulting crude product is purified on silica (150 g) with cyclohexane/EtOAc 5/1 to afford pure [2-(3'-hydroxy-biphenyl-4-yl)-ethyl]-carbamic acid tert-butyl ester.

MS (ESI+): 336 [M+Na]; Rf: (EtOAc/hexane=1/2): 0.28.

Stage 4.2: {2-[3'-(2-Chloro-pyrimidin-4-yloxy)-biphenyl-4-yl]-ethyl}-carbamic acid tert-butyl ester A mixture of [2-(3'-hydroxy-biphenyl-4-yl)-ethyl]-carbamic acid tert-butyl ester (552 mg), 2,4-dichloropyrimidine (189 mg) and potassium carbonate (252 mg) in DMF (10 ml) is stirred at rt for 20 h. This mixture is quenched with brine and extracted twice with EtOAc. The combined organic phases are dried over sodium sulfate, the solvent is evaporated and the resulting crude product is purified on silica (60 g) with cyclohexane/EtOAc 80/20 to afford pure {2-[3'-(2-chloro-pyrimidin-4-yloxy)-biphenyl-4-yl]-ethyl}carbamic acid tert-butyl ester.

MS (ESI+): 448 [M+Na]; Rf: (EtOAc/hexane=1/2): 0.35.

Stage 4.3: {2-[3'-(2-Cyano-pyrimidin-4-yloxy)-biphenyl-4-yl]-ethyl}-carbamic acid tert-butyl ester A mixture of {2-[3'-(2-chloro-pyrimidin-4-yloxy)-biphenyl-4-yl]-ethyl}carbamic acid tert-butyl ester (150 mg), potassium cyanide (76 mg) and 1,4-diazabicyclo[2,2,2]octane (13 mg) in water (0.4 ml) and DMSO (2 ml) is left at 5° C. for 4 h. This mixture is acidified with AcOH to pH 4-5, quenched with brine and extracted twice with diethyl ether. The combined organic phases are dried over sodium sulfate, the solvent is evaporated and the crude product is purified on silica (15 g) with cyclohexane/EtOAc=5/1 to afford pure {2-[3'-(2-cyano-pyrimidin-4-yloxy)-biphenyl-4-yl]-ethyl}carbamic acid tert-butyl ester.

MS (ESI+): 439 [M+Na]; Rf: (EtOAc/hexane=1/2): 0.26.

Example 5

4-[3-(4-Aminomethyl-benzyloxy)-phenoxy]-pyrimidine-2-carbonitrile, Salt with Formic Acid {4-[3-(2-Cyano-pyrimidin-4-yloxy)-phenoxymethyl]-benzyl}carbamic acid tert-butyl ester (68 mg; 0.157 mmol) (see Example 5; step 5.3) is dissolved at rt in formic acid (1.5 mL) under an atmosphere of argon and stirred for 65 min. The reaction mixture is freed from the solvent under reduced pressure at rt. The residue is taken up into dioxane (20 mL) and lyophilized to obtain the title compound as formate salt; ES-MS [M+H]$^+$; m/z=333 (M+H)$^+$; HPLC: $^A t_{Ret}$=3.49 min (System 1).

The starting materials are prepared as follows:

Stage 5.1: 3-(2-Chloro-pyrimidin-4-yloxy)-phenol

Sodium hydroxide (1.68 g; powder 98% pure; 40 mmol) is dissolved in water (30 mL), cooled to 0° C. and treated with benzene-1,3-diol (4.4 g; 40 mmol). Within 15 min, 2,4-dichloropyrimidine (5.95 g; 40 mmol) dissolved in acetone (50 mL) is added dropwise, keeping the reaction temperature below 5° C. After 15 min at 0° C., the ice bath is removed and the reaction kept stirring for additional 17.5 h. After filtering off the precipitate, the solvent is removed under reduced pressure. The residual oil is taken up into EtOAc, washed with sodium bicarbonate solution (10%), water and brine and dried over $Na_2SO_4$. After filtering, the crude product is isolated as an oil and purified by flash chromatography over silica gel (eluting with $CH_2Cl_2$/MeOH; 0-5%) to give the title compound of Stage 5.1 as a beige solid; ES-MS: [M+H]$^+$; m/z=223; $R_f$ ($CH_2Cl_2$/MeOH 9:1)=0.57; HPLC: $^A t_{Ret}$=3.50 min.

Stage 5.2: {4-[3-(2-Chloro-pyrimidin-4-yloxy)-phenoxymethyl]-benzyl}carbamic acid tert-butyl ester Under an atmosphere of argon, 3-(2-chloro-pyrimidin-4-yloxy)-phenol (177 mg; 0.8 mmol; Stage 5.1) is dissolved in DMF (4 mL), followed by addition of $Cs_2CO_3$ (1.30 g; 4.0 mmol) and stirring is continued for 20 min. (4-Chloromethyl-benzyl)-carbamic acid tert-butyl ester (203 mg; 0.8 mmol) and tetrabutyl ammonium iodide (20 mg) are added, and the reaction is continued for another 1 h 50 min. The reaction mixture is poured onto brine, taken up into EtOAc, washed with water and brine and dried ($Na_2SO_4$). After filtration, the solvent is removed under reduced pressure and the crude product is purified by flash chromatography over silica gel (eluting with Hexane/EtOAc 80:20) to give the title compound of Stage 5.2 as an oil; ES-MS: [M+H]$^+$; m/z=442; $R_f$ (Hexane/EtOAc 1:1)=0.50; HPLC: $^A t_{Ret}$=5.29 min.

Stage 5.3: {4-[3-(2-Cyano-pyrimidin-4-yloxy)-phenoxymethyl]-benzyl}carbamic acid tert-butyl ester {4-[3-(2-Chloro-pyrimidin-4-yloxy)-phenoxymethyl]-benzyl}carbamic acid tert-butyl ester (126 mg; 0.285 mmol; Stage 5.2), DABCO (16 mg; 0.143 mmol) and KCN (38 mg; 0.584 mmol) are dissolved in DMSO/water 4:1 (4 mL) at rt under an atmosphere of argon. After 20 min, more DABCO (16 mg) is added and the reaction is continued for a total of 1 h 50 min. The reaction mixture is poured onto brine, taken up into EtOAc, washed with water and brine and dried ($Na_2SO_4$). After filtration, the solvent is removed under reduced pressure and the crude product is purified by flash chromatography over silica gel (eluting with Hexane/EtOAc 80:20) to give the title compound of Stage 5.3 as an oil; ES-MS: [M−H]$^-$; m/z=431; R$_f$ (Hexane/EtOAc 1:1)=0.45; HPLC: $^A$t$_{Ret}$=5.19 min.

Example 6

4-[3-(2-Cyano-pyrimidin-4-yloxy)-phenoxymethyl]-benzamidine, Salt with TFA

Under an atmosphere of argon, 4-[3-(2-chloro-pyrimidin-4-yloxy)-phenoxymethyl]-benzamidine (46 mg; 0.13 mmol; Stage 6.2) is dissolved in DMF/water 5:1 (1.2 mL) followed by addition of DABCO (7 mg; 0.065 mmol) and KCN (17 mg; 0.267 mmol) at rt. After stirring for 3.5 h at rt, the reaction mixture is adjusted to pH 6 using diluted acetic acid and the crude mixture is purified on column chromatography on reversed phase silica (Lichroprep RP18; 15-25 μm), eluting with H$_2$O (0.1% TFA), followed by H$_2$O/acetonitrile (40/60) (0.1% TFA in both). After concentration of the solution, the title compound is isolated by lyophilization as TFA salt; ES-MS: [M+H]$^+$; m/z=346; HPLC: $^A$t$_{Ret}$=3.44 min.

The starting materials are prepared as follows:

Stage 6.1: 4-[3-(2-Chloro-pyrimidin-4-yloxy)-phenoxymethyl]-benzonitrile

The title compound is prepared as described in Example 5; Stage 5.2, using 4-chloromethyl-benzonitrile instead of (4-chloromethyl-benzyl)-carbamic acid. Title compound: ES-MS: [M+H]$^+$; m/z=338; R$_f$ (Hexane/EtOAc 1:1)=0.43; HPLC: $^A$t$_{Ret}$=4.98 min.

Stage 6.2: 4-[3-(2-Chloro-pyrimidin-4-yloxy)-phenoxymethyl]-benzamidine

4-[3-(2-Chloro-pyrimidin-4-yloxy)-phenoxymethyl]-benzonitrile (169 mg; 0.5 mmol; Example 6; Stage 6.1) is dissolved in CHCl$_3$ (5 mL) and EtOH (0.5 mL) and cooled to 0° C. At this temperature, HCl gas is gently bubbled through during 20 min. The reaction mixture is kept at 4-5° C. for 72 h. After this time, pentane (10 mL) is added and stirring is continued for 1 h at 0° C. The supernatant is removed by decantation, and the residue (intermediate product) is suspended in MeOH (2 mL). At 0° C., NH$_3$ (0.375 mL 2M solution in MeOH; 0.75 mmol) and NH$_4$Cl (27 mg; 0.5 mmol) are added and the mixture is stirred at rt for 5 h 15 min. More NH$_3$ (0.375 mL 2M solution in MeOH; 0.75 mmol) is added, as well as diethyl ether. After removal of the solvents under reduced pressure, the residue is taken up in EtOAc/water, extracted with water and brine and dried (Na$_2$SO$_4$). After filtration, the solvent is removed under reduced pressure to obtain a small amount of the title compound as free base. Since most of the product is in the aqueous layer, the latter is lyophilized and the residue purified twice over reversed phase silica (Lichroprep RP18; 15-25 μm), eluting with H$_2$O/acetonitrile (0->43%) (0.1% TFA in both). After concentration of the solution, the title compound is isolated by lyophilization as TFA salt; ES-MS: [M+H]$^+$; m/z=355; HPLC: $^A$t$_{Ret}$=3.43 min.

Example 7

3-[3-(2-Cyano-pyrimidin-4-yloxy)-phenoxymethyl]-benzamidine, Salt with TFA

The title compound is prepared as described in Example 6, using 3-[3-(2-chloro-pyrimidin-4-yloxy)-phenoxymethyl]-benzamidine (Stage 7.2) instead of the 4-analogue. The title compound is isolated as TFA salt: ES-MS: [M+H]$^+$; m/z=346; HPLC: $^A$t$_{Ret}$=3.43 min.

The starting materials are prepared as follows:

Stage 7.1: 3-[3-(2-Chloro-pyrimidin-4-yloxy)-phenoxymethyl]-benzonitrile

The title compound is prepared as described in Example 5; Stage 5.2, using 3-bromomethyl-benzonitrile instead of (4-chloromethyl-benzyl)-carbamic acid. The title compound is obtained: ES-MS: [M+H]$^+$; m/z=338; R$_f$ (EtOAc)=0.44; HPLC: $^A$t$_{Ret}$=4.96 min.

Stage 7.2: 3-[3-(2-Chloro-pyrimidin-4-yloxy)-phenoxymethyl]-benzamidine

The title compound is prepared as described in Example 6; Stage 6.2, using 3-[3-(2-Chloro-pyrimidin-4-yloxy)-phenoxymethyl]-benzonitrile (Example 7; Stage 7.1) instead of the 4-analogue. The title compound is obtained as TFA salt: ES-MS: [M+H]$^+$; m/z=355; HPLC: $^A$t$_{Ret}$=3.41 min.

Example 8

Dry-filled Capsules 5000 capsules, each comprising as active ingredient 0.25 g of one of the compounds of formula I mentioned in the preceding Examples, are prepared as follows:

| Composition | |
|---|---|
| active ingredient | 1250 g |
| talcum | 180 g |
| wheat starch | 120 g |
| magnesium stearate | 80 g |
| lactose | 20 g |

Preparation process: The mentioned substances are pulverized and forced through a sieve of 0.6 mm mesh size. 0.33 g portions of the mixture are introduced into gelatin capsules using a capsule-filling machine.

Example 9

Soft Capsules 5000 soft gelatin capsules, each comprising as active ingredient 0.05 g of one of the compounds of formula I mentioned in the preceding Examples, are prepared as follows:

| Composition | |
|---|---|
| active ingredient | 250 g |
| PEG 400 | 1 liter |
| Tween 80 | 1 liter |

Preparation process: The active ingredient is pulverized and suspended in PEG 400 (polyethylene glycol having an M$_r$ of from approx. 380 to approx. 420, Fluka, Switzerland) and Tween®80 (polyoxyethylene sorbitan monolaurate, Atlas Chem. Ind. Inc., USA, supplied by Fluka, Switzerland) and ground in a wet pulverizer to a particle size of approx. from 1 to 3 μm. 0.43 g portions of the mixture are then introduced into soft gelatin capsules using a capsule-filling machine.

The invention claimed is:

1. A compound of the formula I,

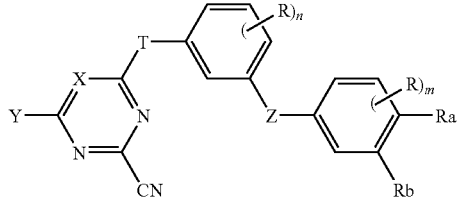

wherein X is; CH or CR

Y is hydrogen or $C_1$-$C_7$-alkyl, $C_3$-$C_{10}$-cycloalkyl, $C_1$-$C_7$-alkyloxy, $C_3$-$C_{10}$-cycloalkyloxy or amino that is unsubstituted or substituted by one or two moieties selected from the group consisting of $C_1$-$C_7$-alkyl and $C_3$-$C_{10}$-cycloalkyl, where each $C_1$-$C_7$-alkyl and $C_3$-$C_{10}$-cycloalkyl mentioned as or forming part of a substituent Y mentioned so far is unsubstituted or substituted by halo, hydroxy, $C_1$-$C_7$-alkoxy, amino, N-mono- or N,N-di-($C_1$-$C_7$-alkyl)amino, nitro or cyano;

Z is absent so that the two bonds binding Z form a single bond or is O—$CH_2$ or NH—$CH_2$;

T is $CH_2$, O or NQ, wherein Q is hydrogen, $C_1$-$C_7$-alkyl, $C_3$-$C_{10}$-cycloalkyl, $C_3$-$C_{10}$-cycloalkyl, phenyl or naphthyl-$C_1$-$C_7$-alkyl;

at least one of Ra and Rb is amino, amino-$C_1$-$C_7$alkyl, hydrazino, amidino, amidino-$C_1$-$C_7$-alkyl, guanidino or guanidino-$C_1$-$C_7$-alkyl, where in each amino, hydrazino, amidino or guanidino mentioned each imino and/or each amino forming part of such a group or being such a group is, independently f the others, unsubstituted or substituted by one or in the case of amino two moieties independently selected from the group consisting of $C_1$-$C_7$-alkyl, phenyl, naphthyl, phenyl- or naphthyl-$C_1$-$C_7$-alkyl, $C_3$-$C_{10}$-cycloalkyl and $C_3$-$C_{10}$-cycloalkyl, while the other is also one of these moieties or is hydrogen or R;

each R if present is, independently of the others, replacing a hydrogen in the corresponding ring in formula I and is selected from the group consisting of $C_1$-$C_7$-alkyl, $C_1$-$C_7$-alkoxy-$C_1$-$C_7$-alkyl, halo-$C_1$-$C_7$-alkyl, phenyl- or naphthyl-$C_1$-$C_7$-alkyl, phenyl, naphthyl, halo, hydroxy, $C_1$-$C_7$-alkyloxy, phenyl- or naphthyl-$C_1$-$C_7$alkyloxy, phenoxy, naphthoyloxy, $C_1$-$C_7$-alkanoyloxy, halo-$C_2$-$C_7$-alkanoyloxy, benzoyloxy, naphthoyloxy, amino that is unsubstituted or substituted by one or two moieties independently selected from the group consisting of $C_1$-$C_7$-alkyl, phenyl-$C_1$-$C_7$alkyl, naphthyl-$C_1$-$C_7$alkyl, $C_1$-$C_7$-alkanoyl, benzoyl naphthoyl, $C_3$-$C_{10}$-cycloalkyl and $C_3$-$C_{10}$-cycloalkyl, carboxy, $C_1$-$C_7$-alkoxycarbonyl, phenyl-$C_1$-$C_7$-alkoxycarbonyl naphthyl-$C_1$-$C_7$-alkoxycarbonyl, $C_3$-$C_{10}$-cycloalkoxycarbonyl, $C_3$-$C_{10}$-cycloalkoxycarbonyl carbamoyl, N-mono- or N,N-di-($C_1$-$C_7$-alkyl, phenyl-$C_1$-$C_7$-alkyl, naphthyl-$C_1$-$C_7$-alkyl, $C_1$-$C_7$-alkanoyl, benzoyl, naphthoyl, $C_3$-$C_{10}$-cycloalkyl and/or $C_3$-$C_{10}$-cycloalkyl)carbamoyl, sulfamoyl, N-mono- or N,N-di-($C_1$-$C_7$-alkyl, phenyl-$C_1$-$C_7$-alkyl, naphthyl-$C_1$-$C_7$-alkyl, $C_3$-$C_{10}$-cycloalkyl and/or $C_3$-$C_{10}$-cycloalkyl)-sulfamoyl, nitro and cyano;

n is 0 to 4; and
m is 0 to 4;
or a salt thereof.

2. A compound of the formula I according to claim 1, wherein

X is CH or CR;

Y is hydrogen or $C_1$-$C_4$-alkyl, $C_3$-$C_8$-cycloalkyl, $C_1$-$C_4$-alkyloxy, $C_3$-$C_8$-cycloalkyloxy or amino that is unsubstituted or substituted by one or two moieties selected from the group consisting of $C_1$-$C_4$-alkyl and $C_3$-$C_8$-cycloalkyl;

Z is absent (so that the two bonds binding Z form a single bond) or is O—$CH_2$ or NH—$CH_2$;

T is $CH_2$, O or NQ, wherein Q is hydrogen, $C_1$-$C_4$-alkyl, $C_3$-$C_8$-cycloalkyl, $C_3$-$C_8$-cycloalkyl, phenyl or naphthyl-$C_1$-$C_4$-alkyl;

at least one of Ra and Rb is amino, amino-$C_1$-$C_4$-alkyl, such as aminomethyl or aminoethyl, hydrazino, amidino, amidino-$C_1$-$C_4$-alkyl, such as amidinomethyl or amidinoethyl, guanidino or guanidino-$C_1$-$C_4$-alkyl, such as guanidinamethyl or guanidinoethyl, where in each amino, hydrazino, amidino or guanidino;

each R if present (that is if n and/or m are 1 to 2, respectively or X is CR) is, independently of the others, replacing a hydrogen in the corresponding ring in formula I and is selected from the group consisting of $C_1$-$C_4$-alkyl, halo, hydroxy, $C_1$-$C_4$-alkyloxy, $C_2$-$C_4$-alkanoyloxy, amino that is unsubstituted or substituted by one or two moieties independently selected from the group consisting of $C_1$-$C_4$-alkyl, phenyl-$C_1$-$C_4$-alkyl, carboxy, $C_1$-$C_4$-alkoxycarbonyl, carbamoyl, sulfamoyl, nitro and cyano;

n is 0 to 2; and
m is 0 to 2;
or a salt thereof.

3. A compound of the formula I according to claim 1, wherein

X is CH;

Y is hydrogen;

Z is absent (so that the two bonds binding Z form a single bond) or is O—$CH_2$;

T is O or NH;

Ra is aminomethyl, 2-aminoethyl, amidino or guanidino and Rb is hydrogen, or

Ra is hydrogen and Rb is aminomethyl, 2-aminoethyl, amidino or guanidino; and each of n and m is zero;

or a salt thereof.

4. A compound of the formula I according to claim 1, selected from the group consisting of:

4-(4'-aminomethyl-biphenyl-3-yloxy)-pyrimidine-2-carbonitrile;

N-[3'-(2-cyano-pyrimidin-4-yloxy)biphenyl-4-yl]guanidine;

[4-(4'-aminoethyl-biphenyl-3-yloxy)-pyrimidine-2-carbonitrile;

4-[3-(4-aminomethyl-benzyloxy)-phenoxy]-pyrimidine-2-carbonitrile; and

4-[3-(2-cyano-pyrimidin-4-yloxy)-phenoxymethyl]-benzamidine, or a salt thereof.

5. A pharmaceutically acceptable salt of a compound of the formula I according to claim 1.

6. A pharmaceutical preparation comprising at least a compound of the formula I, or a pharmaceutically acceptable salt thereof, according to claim 1 and a pharmaceutically acceptable carrier material.

7. A method of treatment of prostrate cancer that depends on cysteine protease activity or responds to modulation of such a cysteine protease, comprising administering a prophylactically or therapeutically effective amount of a compound of formula I, or a pharmaceutically acceptable salt thereof, according to claim 1 to a warm-blooded animal, that is in need of such treatment.

8. A process for the manufacture of a compound of the formula I, or a salt thereof, according to claim 1, comprising:
reacting a compound of the formula II,

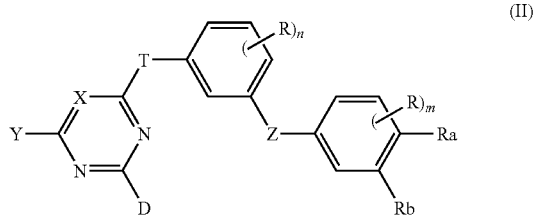

wherein D is a leaving group and X, A, Z, T, T, Ra, Rb, m and n have the meanings given for a compound of the formula I in claim 1, with a cyanide introducing reagent, and transforming an obtainable compound of formula I into a different compound of formula I, transforming a salt of an obtainable compound of formula I into the free compound or a different salt, transforming an obtainable free compound of formula I into a salt thereof, and/or separating an obtainable mixture of isomers of a compound of formula I into individual isomers;

where in any starting material of the formula II functional groups that shall not take part in the manufacturing and/or a conversion reaction may be present in protected form and protecting groups are removed to obtain a compound of the formula I.

* * * * *